United States Patent [19]

Freed

[11] 4,400,511
[45] Aug. 23, 1983

[54] 2-SUBSTITUTED OCTAHYDROPYRROLO(1,2-A)-PYRAZINE-3-CARBOXYLIC ACIDS

[75] Inventor: Meier E. Freed, Paoli, Pa.

[73] Assignee: American Home Products Corporation, New York, N.Y.

[21] Appl. No.: 375,858

[22] Filed: May 7, 1982

[51] Int. Cl.³ .................. C07D 487/04; A61K 31/495
[52] U.S. Cl. ..................................... 544/349; 424/250
[58] Field of Search ......................... 544/349; 424/250

[56] References Cited

U.S. PATENT DOCUMENTS 3,531,485  9/1970  Freed .................................. 544/349
4,291,163  9/1981  Wright ............................... 546/164
4,294,832  10/1981  Yoneda ............................. 424/258

FOREIGN PATENT DOCUMENTS 50-88093  7/1975  Japan ................................. 544/349

Primary Examiner—Donald G. Daus

Assistant Examiner—G. Hendricks
Attorney, Agent, or Firm—Richard K. Jackson

[57] ABSTRACT

The compounds

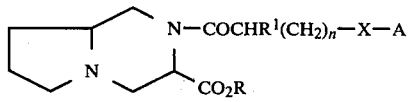

where
R is hydrogen, alkyl, phenylalkyl or dialkylamino alkyl;
R¹ is hydrogen, alkyl or phenyl;
X is —S— or —NH—
A is hydrogen, acyl, aroyl, alkyl or substituted alkyl in which the substituent is alkoxycarbonyl or phenylalkyl;
n is 0, 1 or 2;

or a pharmaceutically acceptable salt thereof are antihypertensive agents of the ACE inhibitor type.

6 Claims, No Drawings

2-SUBSTITUTED OCTAHYDROPYRROLO(1,2-A)-PYRAZINE-3-CARBOXYLIC ACIDS

DESCRIPTION OF THE INVENTION

In accordance with this invention there is provided a group of compounds of the formula:

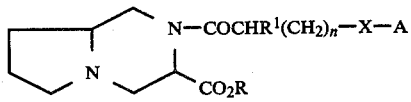

in which:
R is hydrogen, alkyl of 1 to 6 carbon atoms, phenylalkyl of 7 to 12 carbon atoms, or dialkylaminoalkyl when each alkyl group contains 1 to 6 carbon atoms;
$R^1$ is hydrogen, alkyl of 1 to 6 carbon atoms or phenyl;
X is —S— or —NH—;
A is hydrogen, alkyl of 1 to 6 carbon atoms, alkoxycarbonylalkyl in which each alkyl moiety is of 1 to 6 carbon atoms, phenylalkyl of 7 to 12 carbon atoms, phenyl(alkoxycarbonyl)alkyl in which each alkyl group contains from 1 to 6 carbon atoms, alkanoyl of 2 to 7 carbon atoms, benzoyl or naphthoyl;
and n is one of the integers 0, 1 or 2;
or a pharmaceutically acceptable salt thereof. The compounds of this invention reduce blood pressure in animals. They function as inhibitors of angiotensin converting enzyme in that they block the removal by C-terminal cleavage of the histidyl[9]-leucine[10] dipeptide from the decapeptide angiotensin I which yields the strong pressor octapeptide angiotensin II.

The pharmaceutically acceptable salts of the compunds of this invention are produced from inorganic or organic acids such as hydrochloric, hydrobromic, sulfuric, phosphoric, nitric, formic, acetic, propionic, oxalic, succinic, glycollic, lactic, malic, tartaric, citric, ascorbic, maleic, phenylacetic, benzoic, para-aminobenzoic, salicylic, methanesulfonic acids, and the like. Similarly, where R is hydrogen, pharmaceutically acceptable salts of the carboxyl group may be derived from either inorganic or organic bases to yield ammonium salts; alkali metal salts (sodium, potassium, etc.); alkaline earth salts, preferably calcium or magnesium, lower alkylamine salts; di(lower)alkylamine salts; tri(lower)alkylamine salts and the corresponding omega-hydroxy analogues (e.g. methylamine, ethylamine, propylamine, dimethylamine, diethylamine, dipropylamine, trimethylamine, triethylamine, tripropylamine, di(hydroxyethyl)amine, and the like). Similarly more complex amines which are employed in depot administration for slow release into the body, such as N,N[1]-dibenzylethylenediamine, are applicable bases for pharmaceutically acceptable salt formation. The pharmaceutically acceptable salts are produced by conventional techniques well-known in the art.

The compounds of this invention are produced from 1,4-diazabicyclo[4.3.0]nonane-3-carboxylic acid by various techniques such as by acylation with an appropriately S or N protected acid or acid halide followed by removal of the protecting group and introduction of the A substituent as desired. Thus, 1,4-diazabicyclo[4.3.0]nonane-3-carboxylic acid may be acylated with 3-benzoylthio-2-methylpropionyl chloride followed by removal of the benzoyl protecting group to afford the free mercaptan which may be then modified, if desired, with other A substituents. Similarly, 1,4-diazabicyclo[4.3.0]nonane-3-carboxylic acid may be acylated with an N-protected α-amino acid, such as N-carbobenzoxy alanine, employing a coupling agent conventionally employed in the polypeptide art for production of the peptide linkage, such as dicyclohexylcarbodiimide, followed by removal of the N-protecting group and introduction of the desired A substituent as by reductive alkylation with ethyl 2-oxo-4-phenylbutyrate in the presence of sodium cyanoborohydride.

In those compounds where A and R are hydrogen, ring closure to form the corresponding thiaza or diaza heterocyclic structure may be accomplished by conventional activation of the carboxyl group, e.g. as an activated ester, mixed anhydride, acylhalide or with a coupling reagent such as a carbodiimide, where appropriate. Of the available carbodiimide coupling agents, N,N'-dicyclohexylcarbodiimide (DCC) is preferred because of the facility of the ring closure and ease of removal of the dicyclohexyl urea byproduct. The ring closed diaza or thiaza analogues of the compounds of this invention present the structural formula:

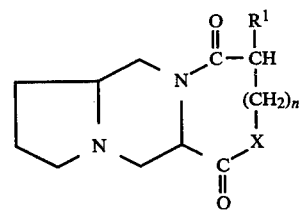

in which $R^1$, X and n have the previously stated definitions. These ring closed analogues possess the same activity profile as the open ring compounds of this invention and may be employed as prodrugs for the same purpose and by the same administration techniques as the open ring compounds.

The 1,4-diazabicyclo[4.3.0]nonane-3-carboxylic acid starting material may be prepared by borohydride reduction of benzylpyroglutamide followed by reaction of the product with a 2,3-dibromopropionic acid ester, removal of the benzyl protecting group and subsequent hydrolysis of the ester, thusly:

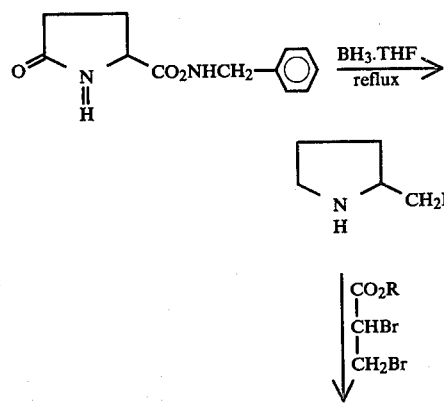

-continued

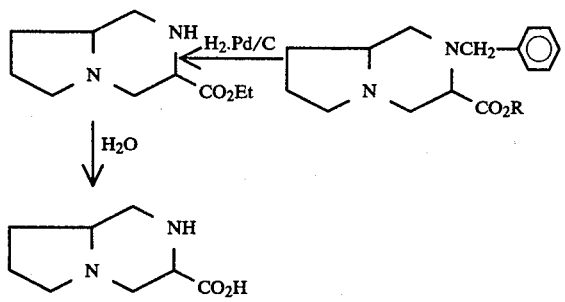

The other reactants employed to produce the compounds of this invention are known or readily preparable by conventional techniques.

The compounds of this invention inhibit the conversion of angiotensin I to angiotensin II, thereby alleviating hypertension caused by the strong pressor action of the latter octapeptide. The compounds are administered to the hypertensive animal in single or divided doses, orally or parenterally, at a dose from about 10 to 150 milligrams per kilograms per day. The preferable dosing regimen provides from about 25 to 100 milligrams per kilogram per day, depending upon the severity of the hypertensive state. Oral administration in solid form by tablet or capsule may be accomplished with the compounds of this invention in neat or pure form, alone or in combination with conventional adjuvants. Similarly, parenteral administration may be accomplished with physiological saline or via suspension in conventional vehicles. In any event, the dosing regimen must be individualized by the attending physician for the patient based upon the severity of the dysfunction.

The activity of the compounds of this invention was established by incubation of hippuryl-L-histidyl-L-leucine at 37° C. with angiotensin converting enzyme by the following procedure:

A crude angiotensin converting enzyme supernatant is obtained by blending 1 g. of rabbit lung acetone powder (Pel-Freez Biologicals) with 35 ml. of 50 mM (buffered) potassium phosphate, pH 8.3 and centrifuging for 45 min. at 40,000 xg.

The specific angiotensin converting enzyme substrate Hippuryl-L-histidyl-L-leucine (HHL-Sigma Chem. Co.) is prepared at 5 mM in 200 mM potassium phosphate buffer containing 757 mM NaCl at pH 8.3.

Incubation for the assay of HHL hydrolysis by angiotensin converting enzyme is carried out in a 37° C. gyrorotary incubator in disposable 13×100 mm tubes. Each 0.25 ml assay mixture contains the following components at the final concentrations: potassium phosphate buffer, 100 mM; NaCl, 300 mM; HHL, 5 mM; and enzyme 0.15 ml (10 mU approx.) added last to initiate the reaction. Zero time controls have 0.25 ml of 2 N HCl added before the enzyme. The timed reactions are terminated with acid at 30 min. similarly and the hippuric acid freed from the substrate is extracted into 1.5 ml of ethylacetate by vortex mixing for 15 sec. After 5 min. centrifugation in a clinical centrifuge, a 1.0 ml aliquot of the ethyl acetate layer is transferred to a clean tube. These aliquots are evaporated to dryness by heating (120° C.) in a Temp-Block module heater.

The hippuric acid is resuspended in 1.0 ml of water, the absorbance at 228 nm is determined, and the amount present is calculated from a standard curve. The amount of hippuric acid × 1.1 (extraction coefficient) × 1.5 (ratio of volumes) × 1 μM hippuric acid/200 μg × 1/30 min = nM hippuric acid released/min. Enzyme activity in the presence of an inhibitor is compared with control activity, and reported as the concentration at which 50 percent of the enzyme activity is inhibited. (Cushman, D. W. and Cheung, H. S., Biochem. Pharmacol. 20 1637 (1971).

In addition, the blood pressure lowering ability of the compounds of this invention was establshed by measuring the systolic pressure of male spontaneously hypertensive rats with a Decker Caudal Plethysmograph. The compounds tested were administered orally and blood pressure was read prior to and at 1.5 hours after drug administration.

As a representative compound of the invention, a $2.66 \times 10^{-7}$ molar concentration of the product of Example 2, infra., inhibited angiotensin converting enzyme by 50 percent in the above described in vitro test and reduced blood pressure in the rat by −22 mm Hg at 1.5 hours in vivo at 50 milligrams dose.

The compounds of this invention contain two chiral centers and when $R^1$ is other than hydrogen, they contain three chiral centers. The isomeric forms of the products may be separated by standard procedures or, by selection of reactants possessing the desired configuration, the form of the product may be controlled. Thus, the several epimers and enantiomers may be isolated by fractional crystallization, high pressure chromatography and other techniques available to the chemist.

The following preparation examples are presented by way of illustration rather than limitation.

EXAMPLE 1

(−)-1,4-Diazabicyclo[4.3.0]nonane-3-carboxylic Acid

Benzyl-(−)-pyroglutamide (60 g.) was suspended in one liter of tetrahydrofuran (THF) and stirred under nitrogen. The mixture was cooled to below 10° C. in an ice bath and one liter of 1 M BH3 THF complex was slowly added. The mixture was stirred for 20 hours at room temperature and then refluxed for 28 hours. The reaction mixture was then cooled and 200 milliliters of methanol was added dropwise. The solvent was then removed and the residue dissolved in 2 N HCl and warmed in a steam bath for one hour. The solution was then cooled and filtered through Cellite®, basified with 50 percent NaOH, extracted with diethyl ether and the extract was washed with brine. The solution was dried and the solvent was removed to afford 2-benzylaminomethylpyrrolidine (64.2 g.) as a viscous oil.

To 60 g. of (−)benzylaminomethylpyrrolidine in 500 milliliters of lotuene was added 100 milliliters toluene containing 62 g. of ethyl 2,3-dibromopropionate. An exothermic reaction occured. The reaction solution was cooled to 20°–25° C. and 100 milliliters of triethylamine was added. The solution was then warmed to 80°–90° C. for 3 hours and then it was cooled, filtered, the solvent removed and the residue dissolved in diethyl ether and washed with brine. The solution was dried and the diethyl ether removed. The residue was distilled; b.p. 150°–155° C./0.3 mm Hg, to yield 51 g. of (−)ethyl 4-benzyl-1,4-diazabicyclo[4.3.0-]nonane-3-carboxylate in conjunction with another material detected on thin layer chromatography. The product was chromatographed on CC-7 silica gel (1 percent MeOH:ethyl acetate) and the slower moving material recovered as purified product.

(−)Ethyl 4-benzyl-1,4-diazabicyclo[4.3.0]nonane-3-carboxylate (23 g.) was dissolved in 8 milliliters of ethanol and acidified to pH 2 with dry HCl. The solution was added to 3.5 g. of Pd/C (10%) in 30 milliliters of ethanol and shake under hydrogen. Hydrogen uptake was 7 psi. The reaction mixture was filtered and the solvent was removed. The residue was washed with diethylether, dissolved in a minimum amount of water and the solution was saturated with $K_2CO_3$. The free base was then extracted and washed with water, dried and the solvent removed to yield 14 g. (−)ethyl 1,4-diazabicyclo[4.3.0]nonane-3-carboxylate.

Three grams of the product of the preceding paragraph was dissolved in 100 milliliters of water and refluxed overnight. The water was removed, the residue washed with diethyl ether and recrystallized from ethanol to yield the title compound, m.p. 230°–233° C. dec. yield 2.37 g.

EXAMPLE 2

4-(3-benzoylthio-2-methylpropionyl)-1,4-diazabicyclo[4.3.0]nonane-3-carboxylic Acid To a cold solution of (−)1,4-diazabicyclo[4 3 0]nonane-3-carboxylic acid (2.38 g., 0.014 mole), in 10 ml of water, stirred and cooled to 5° C., was added sufficient 50% sodium hydroxide to bring the pH to 9.5. A solution of 3-benzoylthio-2-methylpropionoyl chloride (3.5 g. 0.0144 mole) in 25 ml of toluene was added dropwise to this aqueous solution. Sodium hydroxide solution was added as needed to maintain the pH between 7.5–9.5. The reaction mixture was stirred 48 hours at 5° C. The pH of the solution was adjusted to 3–3.5 with hydrochloric acid. The solution was extracted with diethyl ether to remove impurities. The aqueous solution was taken to dryness at reduced pressure (5 mm), leaving 0.75 g of light brown crysals, m.p. 108°–112° C.; $[\alpha]_D^{25} = -83.44$ (0.935% in methanol).

Analysis for: $C_{19}H_{24}N_2O_4HCl\ H_2O$. Calculated: C, 52.92; H, 6.31; N, 6.50; Cl, 8.23. Found: C, 51.35; H, 6.16; N, 6.63; Cl, 9.96.

EXAMPLE 3

4-(3-mercapto-2-methylpropionyl)-1,4-diazabicyclo[4.3.0]nonane-3-carboxylic Acid By allowing a solution of (−)4-(3-benzoylthio-2-methylpropionyl)-1,4-diazabicyclo[4.3.0]nonane-3-carboxylic acid in ammoniacal methanol to stand at 25° C. for 4–8 hours the title compound is obtained.

EXAMPLE 4

4-(3-benzoylthiopropionyl)-1,4-diazabicyclo[4.3.0]nonane-3-carboxylic Acid

By treating a solution of 1,4-diazabicyclo[4.3.0]nonane-3-carboxylic acid with 3-benzoylpropionyl chloride in the manner of example 2, one obtains the title compound.

EXAMPLE 5

4-(3-mercaptopropionyl)-1,4-diazabicyclo[4.3.0]nonane-3-carboxylic Acid

In the manner of example 3, 4-(3-benzoylthiopropionyl)-1,4-diazabicyclo[4.3.0]nonane is treated with ammoniacal methanol to give the title compound.

EXAMPLE 6

(−)4-[2-[[1-(ethoxycarbonyl)-3-phenylpropyl]amino]-1-oxopropyl]-1,4-diazabicyclo[4.3.0]nonane-3-carboxylic Acid Treat a solution of (−)-1,4-diazabicyclo[4.3.0]nonane-3-carboxylic acid with (−) N-benzyloxycarbonyl (Cbz) alanine and dicyclohexylcarbodiimide to yield Cbz-2-aminopropionyl-(−)-1,4-diazobicyclo[4.3.0]nonane-3-carboxylic acid. Hydrogenolysis of the product gives 4((−)-2-aminopropionyl-)(−)1,4-diazabicyclo[4.3.0]nonane-3-carboxylic acid which, when treated with ethyl 2-oxo-4-phenylbutyrate in the presence of excess sodium cyanoborohydride will provide the title compound.

What is claimed is:

1. A compound of the formula

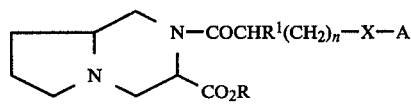

in which
R is hydrogen, alkyl of 1 to 6 carbon atoms, phenylalkyl of 7 to 12 carbon atoms, or dialkylaminoalkyl where each alkyl group has 1 to 6 carbon atoms;
$R^1$ is hydrogen, alkyl of 1 to 6 carbon atoms or phenyl;
X is —S— or —NH—;
A is hydrogen, alkyl of 1 to 6 carbon atoms, alkoxycarbonylalkyl in which each alkyl moiety has 1 to 6 carbon atoms, phenylalkyl of 7 to 12 carbon atoms, phenyl(alkoxycarbonyl)alkyl in which each alkyl group has 1 to 6 carbon atoms, alkanoyl of 2 to 7 carbon atoms, benzoyl or naphthoyl;
and n is one of the integers 0, 1 or 2 or a pharmaceutically acceptable salt thereof.

2. The compound of claim 1 which is 4-(3-benzoylthio-2-methylpropionyl)-1,4-diazabicyclo[4.3.0]nonane-3-carboxylic acid or a pharmaceutically acceptable salt thereof.

3. The compound of claim 1 which is 4-(3-mercapto-2-methylpropionyl)-1,4-diazabicyclo[4.3.0]nonane-3-carboxylic acid or a pharmaceutically acceptable salt thereof.

4. The compound of claim 1 which is 4-(3-benzoylthiopropionyl)-1,4-diazabicyclo[4.3.0]nonane-3-carboxylic acid or a pharmaceutically acceptable salt thereof.

5. The compound of claim 1 which is 4-(3-mercaptopropionyl)-1,4-diazabicyclo[4.3.0]nonane-3-carboxylic acid or a pharmaceutically acceptable salt thereof.

6. The compound of claim 1 which is 4-[2-[[1-(ethoxycarbonyl)-3-phenylpropyl]amino]-1-oxopropyl]-1,4-diazabicyclo[4.3.0nonane-3-carboxylic acid or a pharmaceutically acceptable salt thereof.

* * * * *